United States Patent
Gehin-Delval et al.

(10) Patent No.: US 8,859,018 B2
(45) Date of Patent: Oct. 14, 2014

(54) DELIVERY CARRIER FOR ANTIMICROBIAL ESSENTIAL OILS

(75) Inventors: Cecile Gehin-Delval, Les Hopitaux Neufs (FR); Corinne Appolonia Nouzille, Lausanne (CH); Seow Leng Ng, Singapore (SG)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 13/991,330

(22) PCT Filed: Nov. 24, 2011

(86) PCT No.: PCT/EP2011/070941
§ 371 (c)(1),
(2), (4) Date: Jun. 3, 2013

(87) PCT Pub. No.: WO2012/072488
PCT Pub. Date: Jun. 7, 2012

(65) Prior Publication Data
US 2013/0259959 A1    Oct. 3, 2013

(30) Foreign Application Priority Data
Dec. 3, 2010  (EP) .................................... 10193722

(51) Int. Cl.
| | | |
|---|---|---|
| A61K 36/752 | (2006.01) | |
| A61K 36/8962 | (2006.01) | |
| A61K 36/268 | (2006.01) | |
| A61K 36/00 | (2006.01) | |
| A01N 65/00 | (2009.01) | |
| A23L 3/3472 | (2006.01) | |
| A01N 25/04 | (2006.01) | |

(52) U.S. Cl.
CPC ................ *A01N 25/04* (2013.01); *A01N 65/00* (2013.01); *A23L 3/3472* (2013.01)

USPC ........... 424/736; 424/745; 424/754; 424/756; 424/725

(58) Field of Classification Search
None
See application file for complete search history.

(56) References Cited

U.S. PATENT DOCUMENTS 7,854,936 B2 * 12/2010 Bishop et al. ............ 424/195.15

FOREIGN PATENT DOCUMENTS

| WO | 03028451 | 4/2003 |
|---|---|---|
| WO | 2005110370 | 11/2005 |
| WO | 2007060174 | 5/2007 |
| WO | WO 2008023387 A2 * | 2/2008 |
| WO | 2008028278 | 3/2008 |

OTHER PUBLICATIONS

Sulochanamma et al, Stabilization of flavour volatiles of basil (*Ocimum basilicum* L.) Journal of Food Science and Technology (2009), 46(1), 54-57.*

Holley et al. "Improvement in shelf-life and safety of perishable foods by plant essential oils and smoke antimicrobials" Food Microbiology, vol. 22 (2005), pp. 273-292.

\* cited by examiner

*Primary Examiner* — Qiuwen Mi
(74) *Attorney, Agent, or Firm* — K&L Gates LLP

(57) ABSTRACT

The present invention relates to a use of an emulsion comprising an antimicrobial essential oil, acacia gum and water for improving the antimicrobial effect of the essential oil in an aqueous composition, particularly in a food or beverage composition. Further, the invention relates to a process to improve the antimicrobial effect of an essential oil, and aqueous compositions comprising an emulsion of an antimicrobial essential oil, acacia gum and water.

7 Claims, 1 Drawing Sheet

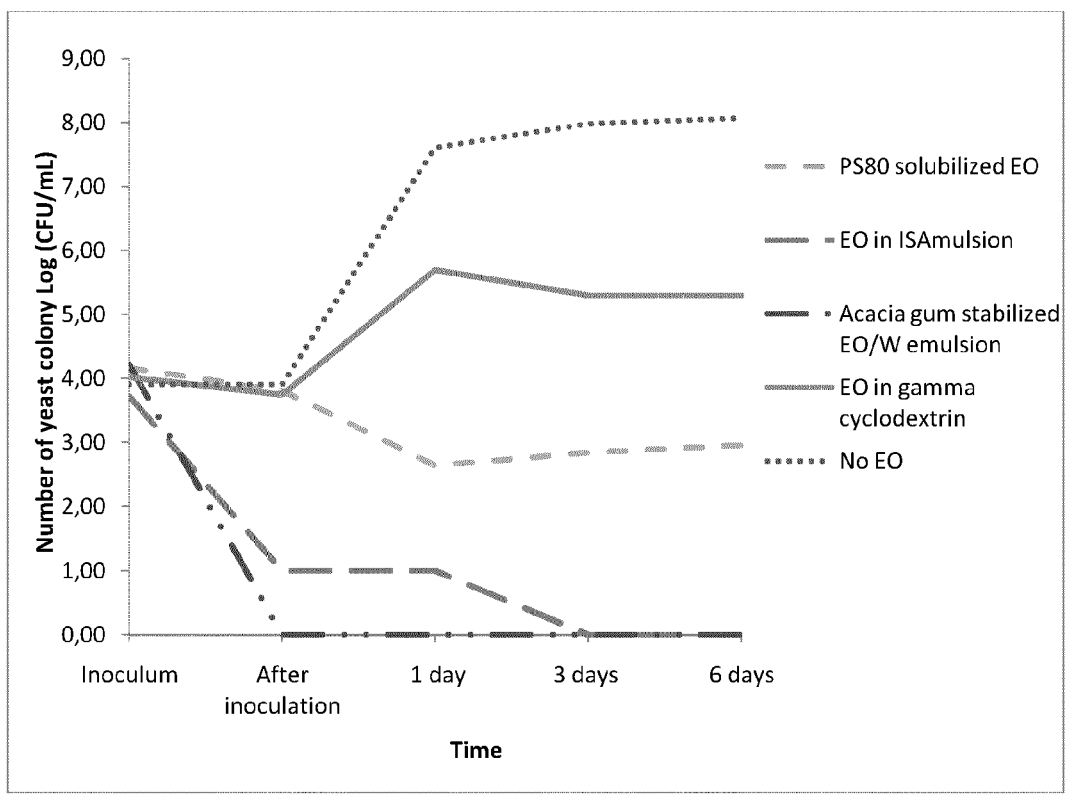

DELIVERY CARRIER FOR ANTIMICROBIAL ESSENTIAL OILS

CROSS REFERENCE TO RELATED APPLICATIONS

The present application is a National Stage of International Application No. PCT/EP2011/070941, filed on Nov. 24, 2011, which claims priority to European Patent Application No. 10193722.5, filed Dec. 3, 2010, the entire contents of which are being incorporated herein by reference.

The present invention relates to a use of an emulsion comprising an antimicrobial essential oil for improving the antimicrobial effect of the essential oil in an aqueous composition. Embodiments of the present invention relate to processes for improving the antimicrobial effect of an essential oil, and to a composition comprising said emulsion.

Microbial contamination of food products can be a considerable health risk to consumers. It may lead for example to heavy gastro-intestinal disorders and is also the suspected cause of 'summer-influenza' which is associated with sickness, emesis, diarrhea and ague. Harmful microorganisms may also contain or excrete strong poisons which may lead to perilous contamination, for example meat poisoning causing botulism. In certain cases, the microorganism can also be carcinogenic, e.g. from mycotoxins of special moulds.

Such spoilage of food or food poisoning is usually prevented by using a combination of different food safety hurdles (also called multi-hurdle system), such as temporary heating of a food product, reducing its water activity, chilled storage and distribution of food products, the addition of chemical preservatives to the products etc., which inhibit or completely destroy undesired microorganisms such as certain bacteria, yeasts and moulds.

Thereby, spoilage of food products by yeasts and moulds is a major concern for the food industry and their growth is mostly prevented by chemical agents such as sorbic, propionic and benzoic acid, or their respective salts. It has been reported that some strains of *Saccharomyces cerevisiae* yeast have multiple resistance to both physical treatment and chemical preservatives.

Further, chemical preservatives which are legally approved and commonly used may still be harmful to some consumers. For instance, benzoic acid and sorbic acid may cause allergies, while sulphite, sulphurous acid and sulphur dioxide may have further deleterious effects. Further, certain chemical preservatives may also release carcinogenic compounds when heated.

Hence, the reduction of such chemical preservatives and salts in food products has been identified as an important consumer need.

There is thus a tendency to look for harmless alternatives which can be used in food products. Amongst these, spices and/or extracts from various plants or fruits have proven to be effective antimicrobial agents. For instance, Weiss J. et al. in Journal of Food Protection, Vol. 68, No. 12, 2005, p. 2559-2566 and in Journal of Food Protection, vol. 68, No. 7, 2005, p. 1359-1366 describe the antimicrobial effect of essential oil components.

Therefore, the use of an essential oil as an antimicrobial agent in a food product could be a consumer friendly alternative to the use of chemical preservatives.

However, essential oils are mostly hydrophobic, i.e. do not mix with water, and cannot be easily solubilised or dispersed in aqueous based food systems. Therefore, essential oils need to be solubilised or encapsulated by a delivery carrier or system in order to make them applicable in water-based food systems.

WO2008/017580 proposes methods for improving the microbiological safety and stability of foods by the use of food-grade micelles that encapsulate antimicrobial agents. Particularly, the use of polyoxyethylene sorbitan monooleate (Admul T 80 K) micelles to solubilise essential oils was disclosed. Trials revealed an inhibition with such solubilised essential oils of for example *Lactobacillus buchneri, E. coli, Salmonella* spp., *Staphylococcus*, and *Listeria*.

WO2003/028451 discloses microbiocidal aqueous formulations comprising an effective amount of an essential oil together with a stabilizer, emulsifier or encapsulation agent. Thereby relatively high concentrations of the essential oils in an aqueous composition are required for obtaining the desired effect. However, there is still a strong flavour and smell impact deriving from such essential oils that can be perceived in a final aqueous product such as for example a food product.

WO2008/028278 discloses an antibacterial coating comprising antimicrobial oils and a hydrophilic polymer. As for the above cited documents, still relatively high concentrations of essential oils are required for obtaining the desired effect. There is still a strong flavour and smell impact deriving from such essential oils that can be perceived in a final product such as for example a food product.

J. F. Ayala-Zavala et al., 2008, in J. Incl Phenom Macrocycl Chem, vol. 60, p. 359-368, and J. F. Ayala-Zavala et al., 2008, in Journal of Food Science, Vol. 73, Issue 4, p. R41-R47, describe that cyclodextrins can be used as carriers to deliver antimicrobial compounds such as anti-microbial essential oils. In this case, the anti-microbial essential oil is complexed with the cyclodextrins due to the amphiphatic nature of the molecule. Possible applications disclosed are to preserve fresh-cut fruits and vegetables.

The problem with using either polyoxyethylene sorbitan micelles or cyclodextrins complexes with an essential oil in a food product is that relatively high concentrations of essential oils are needed in order to have a satisfactory, efficient level of anti-microbial activity in a food end-product. This has as a consequence that a relatively strong flavour and smell impact deriving from the essential oil can be perceived in the final product. This may not be acceptable for a large range of products where one would like to make use of the anti-microbial activity of such essential oils without, however, impacting the normal flavour profile of the product per se. Furthermore, production costs could be kept lower by providing a solution to limit the amount of such costly essential oils needed for obtaining a same anti-microbial protective effect in a food product.

Hence, there is a need in the food industry to find an alternative, improved solution to effectively provide the effect of anti-microbial essential oils to aqueous food products without affecting the inherent flavour and smell profile of said products per se, to reduce the amount of essential oils to be used in order to reduce the costs of such anti-microbial applications, and lastly to find a solution which meets the preferences of consumers for example in regard to the choice and use of ingredients.

The object of the present invention is to provide a solution for a more effective use of essential oils with respect to their anti-microbial activity in aqueous compositions and to overcome at least some of the inconveniences described above, in particular such as reducing the inherent flavour and smell impact of an essential oil to an aqueous composition, e.g. a food composition.

The object of the present invention is achieved by the subject matter of the independent claims. The dependent claims further develop the idea of the present invention.

Accordingly, the present invention provides in a first aspect a novel use of an emulsion comprising an anti-microbial essential oil, acacia gum and water for providing an anti-microbial effect in an aqueous composition.

In a second aspect, the invention relates to a process to improve the antimicrobial effect of an antimicrobial essential oil comprising the steps of: i) emulsifying the essential oil with acacia gum and water to form an emulsion; and ii) adding the emulsion to an aqueous composition to result at a final concentration of the essential oil in the aqueous composition of 0.08 wt % or less, preferably of 0.06 wt % or less, more preferably of 0.04 wt % or less.

In a third aspect, the invention relates to an alternative process to improve the antimicrobial effect of an antimicrobial essential oil comprising the steps of: i) adding the essential oil and acacia gum to an aqueous composition to result at a final concentration of the essential oil in the aqueous composition of 0.08 wt % or less, preferably of 0.06 wt % or less, more preferably of 0.04 wt % or less; and ii) mixing the aqueous composition in order to emulsify the essential oil with the acacia gum.

Yet a further aspect of the invention is an aqueous composition comprising an emulsion of an antimicrobial essential oil, acacia gum and water, wherein the essential oil is present in a concentration of 0.08 wt % or less, preferably of 0.06 wt % or less, more preferably of 0.04 wt % or less, of the aqueous composition.

The present inventors were surprised to find that the use of an emulsion comprising an essential oil with acacia gum significantly improves the anti-microbial effect of the essential oil in an aqueous system over the prior art known uses with e.g. polysorbate PS80 or cyclodextrins. For example, the anti-microbial inhibitory activity against spoilage yeast was improved 10 times and more over the currently known application of essential oil with PS80 micelles. This allows i) at one hand to remarkably improve the microbial food safety if the essential oil is used in the same concentration as with prior art applications, or ii) to re-design the food safety hurdles in a multi-hurdle system in such a way as to reduce for example the use of artificial preservatives which are less desired and still maintaining full microbial safety of a food end-product, or iii) to significantly reduce the amount of essential oil needed in the application and still maintaining full microbial safety of the food product, and thereby reducing the flavour and smell impact of the essential oil to the final product, and reducing costs of production.

BRIEF DESCRIPTION OF THE DRAWINGS

FIG. 1: Impact of a delivery carrier on the effect of an essential oil (EO) on the growth of yeast in malt extract broth (MEB) at pH 5. As a control, growth of yeast in pure MEB at pH 5 is indicated.

DETAILED DESCRIPTION OF THE INVENTION

The present invention pertains to a use of an emulsion comprising an antimicrobial essential oil, acacia gum and water for improving the antimicrobial effect of the essential oil in an aqueous composition, such as e.g. an aqueous food or cosmetic product.

In this context, "improving" means having a better anti-microbial effect than the essential oil per se provided in an aqueous compatible form as for example disclosed in the prior art for either polysorbate PS80 or cyclodextrins as carriers. A better anti-microbial effect pertains to either a lower amount of essential oil which is necessary to inhibit the growth of a same number of undesired micro-organisms, or a same amount of essential oil which is capable of inhibiting the growth of a higher number of such micro-organisms, in comparison to the prior art carrier solutions.

Hence, the advantage of using the emulsion as disclosed herein is that either the amount of the essential oil in for example a multi-hurdle safety system can be reduced, or that the effect is improved as to allow reduction of for example the use of artificial preservatives. Therewith, the quality of an end-product can be improved, undesired flavour and smell eliminated or reduced, and production costs reduced.

The emulsion of the present invention comprises acacia gum. The inventors have found that acacia gum is particularly well suited to be used in emulsions with anti-microbial essential oils for the purpose of the invention. On one hand, acacia gum does well emulsify those oils and provides stable emulsions at concentrations feasible for being used in food and cosmetic applications. On the other hand, the emulsions with acacia gum are such as to allow the essential oils to maintain and exert their anti-microbial effect against undesired micro-organisms in an effective way.

Preferably, the weight ratio of the essential oil versus acacia gum for the emulsion as for the claimed use is from about 1:0.5 to 1:50, preferably from about 1:0.5 to 1:1. This allows a good solubility and efficient anti-microbial use of the essential oil in an aqueous composition.

A good anti-microbial effect can be achieved in an aqueous composition wherein the essential oil is present in a concentration of about 0.15 wt % or less, preferably of about 0.1 wt % or less, more preferably of about 0.08 wt %, 0.06 wt %, 0.04 wt % or less of the total composition. This allows to significantly reducing the amount of an essential oil used in such applications where such oils are usually used at concentrations of about 1.0 wt % to achieve a same anti-microbial effect. This allows reducing food production costs. Further, this solution provides also the advantage that such food products with a lesser amount of total essential oils have a much reduced flavour and/or smell impact of said oil upon consumption of the food end-product which may be much appreciated by the consumer.

The essential oil to be used in the emulsion of the invention can be the oil from a plant material selected from the group consisting of oregano (*origanum*, origan), garlic, ginger, rose, mustard, cinnamon, rosemary, orange, grapefruit, lime, lemon, lemongrass, clove, clove leaf, vanilla, vanillin, mint, tea tree, thyme, grape seed, cilantro, lime, coriander, sage, eucalyptus, lavender, olive, olive leaf, anise, basil, pimento, dill, geranium, eucalyptus, aniseed, camphor, pine bark, onion, green tea, orange, *artemisia herba-alba*, aneth, citrus, marjoram, sage, *ocimum gratissimum, thymus vulgaris, cymbopogon citratus, zingiber officinale, monodora myristica*, and *curcuma longa* or a combination thereof. The inventors have found that for achieving best results, the essential oil is preferably selected from the group consisting of oregano (*origanum*, origan) oil, garlic oil, ginger oil, cinnamon oil, lime oil, lemon oil, lemongrass oil, clove leaf oil and citrus oil, or a combination thereof.

As emulsion of an essential oil for the use of the invention, an emulsion with a self-assembled structure, such as an ISAMULSION can be selected. ISAMULSION refers to an emulsion with a specific nature of oil droplets, where such oil droplets are in a micrometer range and exhibit a nano-sized internal structurisation. A definition and illustration of an ISAMULSION is provided in WO2005/110370. The advantage of using such self-assembly structures is a more controlled delivery and release of the essential oil from the emulsion in an end-product.

The emulsion of the invention can be used in an aqueous composition which is for example a beverage or a food product. Preferably, beverage products are selected from the group consisting of bottled water-based drinks, milk drinks and tea beverages. Food products are preferably selected from the group consisting of sauces, marinades, dressings, condiments, taste makers, soups, desserts and ice cream products. However, it can be envisaged to use the emulsion of the invention also in food supplements and aliments specifically designed for animals.

The emulsion may be used in an aqueous sauce which can be used as a taste maker e.g. for an Asian dish, comprising for example water, spices, salts, vegetables and/or meat. By including 0.05 wt % of a lemongrass essential oil, emulsified with acacia gum in a weight ratio of 1:1, the resulting sauce is more microbiologically shelf-stable. This has been verified and tested in various challenge tests with products which have been inoculated with spoilage yeasts and tested over several weeks.

A further embodiment of the invention is a process to improve the antimicrobial effect of an antimicrobial essential oil comprising the steps of: i) emulsifying the essential oil with acacia gum and water to form an emulsion; and ii) adding said emulsion to an aqueous composition to result at a final concentration of the essential oil in the aqueous composition of 0.08 wt % or less, preferably of 0.06 wt % or less, more preferably of 0.04 wt % or less. This allows to produce the emulsion independently of e.g. geographic locations or timing wise of a final product, and to dose it in an appropriate way and consistently to said final product.

Alternatively, the invention also pertains to a process to improve the antimicrobial effect of an antimicrobial essential oil comprising the steps of: i) adding the essential oil and acacia gum to an aqueous composition to result at a final concentration of the essential oil in the aqueous composition of 0.08 wt % or less, preferably of 0.06 wt % or less, more preferably of 0.04 wt % or less; and ii) mixing the aqueous composition in order to emulsify the essential oil with the acacia gum. This alternative has the advantage that the emulsion of the invention can be produced directly in situ in a product application and does not need separate production facilities to produce the emulsion of the invention. Hence, it is a more cost effective solution.

The weight ratio of the essential oil versus acacia gum in the emulsions generated by the above processes is in the range from about 1:0.5 to 1:50, preferably from about 1:0.5 to 1:1. The inventors have found that such emulsions between an essential oil and acacia gum formed in the range from about 1:0.5 to 1:50 are stable emulsions and can well be used in food product applications. Emulsions below the about 1:0.5 ratio may be less stable, meaning that not all of the essential oil is maintained emulsified with the acacia gum upon prolonged storage. The essential oil will start to separate out again. On the other hand, emulsions above the 1:50 ratio tend not to make use of all of the provided acacia gum. Acacia gum is provided in excess and production costs could be reduced by reducing the excess acacia gum.

A further embodiment of the invention is an aqueous composition comprising an emulsion of an antimicrobial essential oil, acacia gum and water, wherein the essential oil is present in a concentration of 0.08 wt % or less, preferably of 0.06 wt % or less, more preferably of 0.04 wt % or less, of the aqueous composition. The aqueous composition can be a water-based food or beverage product, such as bottled water, a water-based drink, a milk drink and tea beverage, a water-based sauce, a marinade or dressing, a condiment, taste maker, a dehydrated or liquid soup, a dessert, or an ice cream product. Typically, such an aqueous composition is one sensitive to spoilage by microorganisms, such as moulds, yeasts and/or bacteria.

An aqueous product of the invention has the advantage that spoilage by non-desired microorganisms is reduced or eliminated by the anti-microbial activity of the essential oil(s), without that the product in question releases a strong flavour and smell of the essential oil or oils used in the application. At a same time, other safety hurdles such as for example heat treatment or the addition of chemical preservatives are reduced in order to improve the quality of the end-product without compromising on the overall microbial food safety. Costs of production could be reduced as well.

The composition of the invention comprises emulsions of an essential oil and acacia gum in a weight ratio in the range from about 1:0.5 to 1:50, preferably from about 1:0.5 to 1:1.

One composition of the invention is a water-based sauce, a marinade, a dressing, a condiment or a taste maker comprising spices, flavour enhancers, salts, oil, hydrocolloids, vegetables and about 10 wt % of an emulsion of an essential oil from either lemongrass, clove leaf, oregano, garlic, ginger, cinnamon, lime, lemon or citrus oil with acacia gum, and wherein the concentration of the essential oil is 0.06 wt % of the final product or less. Preferably, the composition further comprises meat or fish.

Those skilled in the art will understand that they can freely combine all features of the present invention disclosed herein. In particular, features described for the use of the present invention may be combined with the features of the processes and composition of the present invention and vice versa. Further, features described for different embodiments of the present invention may be combined.

Further advantages and features of the present invention are apparent from the figure, table and the examples.

Example 1

Preparation of Solutions and Materials:
Malt Extract Broth (MEB) is prepared by adding 20 g of malt extract broth powder (from Oxoid, UK) to 1 liter of Millipore water, mixing well, distributing into containers (50 and 100 mL screwable bottles and 200 and 500 mL beakers) and sterilizing by autoclaving at 115° C. for 10 minutes.
The essential oil (EO) used in the following examples is Oregano EO (Origanum essential oil A882) purchased from Givaudan, Switzerland.
Oregano EO solubilised polysorbate 80 (Polysorbate 80 (93781), Fluka) micelles formulated in MEB were prepared as follows.
The polysorbate was dispersed into MEB at 5 wt %. 1 wt % EO was added drop-by-drop and dispersed under magnetic stirring. Then the dispersion was passed through a high pressure homogenizer (1 time at 500 bars) and the pH was adjusted to pH 5 under magnetic stirring. Thereafter, the dispersion was allowed to sit overnight at room temperature.
Oregano EO encapsulated in alpha- or gamma-cyclodextrin (Cavamax W8 Food cyclodextrin from Wacker Fine Chemical, USA) was prepared as follows.
Cyclodextrin was dispersed at 5 wt % in MEB in a sterile bottle. 1 wt % EO was added drop-by-drop under magnetic stirring. The pH was adjusted to pH 5 under magnetic stirring and thereafter allowed to sit overnight at room temperature.

Oregano EO Acacia gum (Eficacia XE-01 acacia gum from Colloïdes Naturels International, France.) stabilized emulsion was prepared as follows.

Acacia gum was dispersed at 1 wt % in MEB in a sterile bottle under magnetic stirring. The EO was added to 1 wt % and dispersed with a homogenizer for 1 minute. Then the dispersion was passed through a high pressure homogenizer (1 time at 500 bars) and the pH was adjusted to pH 5 under magnetic stirring. Thereafter, the dispersion was allowed to sit overnight at room temperature.

ISAmulsion containing oregano EO was prepared as follows.

Unsaturated monoglyceride (Dimodan U, Danisco, USA) was heated to 60° C. and then mixed with the EO in a ratio 1:1 at 60° C. under magnetic stirring. Independently, acacia gum was dispersed at 2 wt % in MEB in a sterile bottle under magnetic stirring. The solution was heated to 80° C. The fat phase of the monoglyceride-EO emulsion was added to the solution to obtain 1 wt % of EO in the final solution. The solution was homogenized for 2 minutes and then passed through a high pressure homogenizer (3 times at 450 bars). The pH was adjusted to pH 5 under magnetic stirring and the dispersion allowed to sit overnight at room temperature.

Microbiological Challenge Test:

One colony of a standard baker's yeast strain (*Saccharomyces cerevisiae*) grown freshly on an agar plate was used to inoculate a tube with 10 ml MEB. The culture was grown over night at 30° C. to stationary phase and diluted thereafter in fresh MEB to a CFU of about $10^6$/ml. Then, 0.5 ml of the diluted yeast culture was used to each inoculate 50 ml of the MEB media comprising 1 wt % of the EO with its different carriers as from above. The cultures were mixed carefully and incubated at 25° C. for testing. A negative control comprising no EO was included.

At day 0, 1, 3 and 6 after start of the challenge test, aliquots were taken from the different cultures, diluted and grown on agar plates for determination of the numbers of remaining viable yeast cells. The results were plotted in FIG. 1.

FIG. 1 shows that the anti-microbial effect of the EO when stabilized in an emulsion with acacia gum is best in comparison to the PS80 solubilised or cyclodextrin using EO delivery system. In fact, it was observed that growth of yeasts was inhibited right after the inoculation with the EO acacia gum emulsion and not detectable anymore. With using the ISAMULSION technology, yeast growth was also drastically reduced and not detectable anymore after 3 days. The use of PS80 and cyclodextrin was clearly much less effective.

Example 2

The microbial challenge test of Example 1 was repeated in the same way, but this time with using different dilutions of the EO delivery system in fresh MEB. Thereby, the minimal concentration of EO necessary to completely inhibit growth of the inoculated yeast cells after 6 days of incubation at 25° C. was determined. The results are depicted in Table 1.

It was evident, that the lowest level of EO needed to inhibit growth of the yeast cells under those conditions was with the EO emulsified with acacia gum. Second best result was achieved with the use of the ISAMULSION technology employing acacia gum. The results showed that an EO acacia gum emulsion is about 50 times more effective in its anti-microbial activity than EO polysorbate 80 micelles, and about 10 times more effective than the solution with alpha-cyclodextrin encapsulation.

TABLE 1

| wt % EO required to inhibit $10^4$ CFU/mL of yeast after 6 days | Delivery carrier | pH |
|---|---|---|
| 0.02-0.04 | EO/W (*acacia* gum stabilized) | 5 |
| 0.1 | ISAmulsion | 5 |
| 0.23 | Alpha-cyclodextrin | 5 |
| 1 | Polysorbate 80 micelles | 5 |
| >1 | Gamma-cyclodextrin | 5 |

The efficacy of the EO acacia gum system has also been tested at pH 3 and pH 8. Basically, the same results were obtained. Hence, the effect of improving the anti-microbial effect of EO with an acacia gum emulsion is independent on the pH of the medium. In a similar way, the efficacy of this system has been tested also at different ionic strength between 0 and 0.4 mol/L of NaCl, without having observed any negative impact on the antimicrobial properties.

Example 3

The anti-microbial efficacy of an EO acacia gum emulsion was evaluated in fresh and aged samples of oyster sauce.

Fresh oyster sauce (OS) tested was the commercial MAGGI Oyster Sauce product from Singapore. The OS was first pasteurized according to standard procedures. After cooling, the samples were divided into 3 groups: A) a negative control group where just 5% of sterilized water was added; B) a positive control group where potassium sorbate (KS) was added to a final concentration of 0.10 wt %; and group C) where a garlic EO acacia gum emulsion (1:1 wt ratio) was added to a final concentration of the EO of 0.12 wt %. Potassium sorbate (E number 202) is widely used as a food preservative and serves here as a positive control. Garlic EO is from Synthite Industries. It was emulsified with acacia gum in the same way as the oregano EO in Example 1.

The three OS samples were stored (i.e. aged) at 30° C. and ca. 65% relative humidity.

Microbiological challenge tests were performed directly after preparation of the OS samples, labelled as 0 month, and then after 3 and 6 months of storage, respectively. The challenge tests were performed in the same way as described in Example 1. However, instead of using *Saccharomyces cerevisiae* as spoilage culture, individual cultures of *Aspergillus niger*, *Penicillium nalgiovense* and *Eurotium amstelodami* were used.

The results showed that:

i) there was no spoilage growth for all samples which were not inoculated with one of the mould strains;

ii) there was visible overgrowth in the samples of group A) which were inoculated with one of the mould strains;

iii) there was no detectable growth of any of the mould strains in the groups B) and C) samples from one week after start of the challenge test to at least 4 weeks thereafter. This was true for all the samples from 0 to 6 months aged OS.

It can be concluded that the anti-microbial efficacy of a garlic EO acacia gum emulsion in an oyster sauce is retained for at least 6 months shelf-life and can protect the oyster sauce from spoilage moulds. The results further show that a 0.12 wt % garlic EO acacia gum emulsion is sufficient to substitute for 0.10 wt % KS, which is a well recognised food preservative. Hence, such EO acacia gum emulsions can serve as natural alternatives for chemical preservatives in food products.

Example 4

MAGGI Oyster Sauce (MOS) at two different dosages of a garlic EO/W (essential oil/water) emulsion, resulting in a 0.06 wt % and 0.12 wt % final EO concentration in the end-product, was produced using a conventional heating process of direct steam injection. MOS containing water with and without potassium sorbate (KS) were also produced using the same method, to serve as experimental controls. All products were thereafter subjected to challenge tests using yeasts and moulds as challenge micro-organisms.

Materials:

The raw materials used for the trials were: Garlic EO from Synthite Industries, Acacia gum from Colloides Naturels Industries, and the raw material for the MOS production from the Nestle Petaling Jaya factory.

Media plates such as Rose-Bengal Chloramphenicol Agar (RBC), Potato Dextrose Agar (PDA), Malt Extract Agar (MEA) and Malt Extract Broth (MEB) were prepared according to manufacturer's instructions. Tryptone Salt 0.1% diluent, Plate Count Agar (PCA), Plate Count Agar (PCA) with Cycloheximide and Dichloran-Glycerol Agar (DG18) media were purchased from Biomedia Laboratories.

Target microorganisms used for the challenge tests (CT) were *Zygosaccharomyces bailii* (yeast), *Aspergillus niger* (mould), *Penicillium nalgiovense* (mould) and *Eurotium amstelodami* (mould).

Method of Production of MOS:

The ingredients for producing MOS were mixed in a tank until homogenous and then pumped to the steam injector steam for mixing with steam. Thereafter, the mixture was pasteurized, the product collected and used for the challenge tests (CT). The same process was used for each of the trials, but with a different concentration of the antimicrobial agents.

Preparation of Moulds for CT:

Stock culture of the mould (mould spores suspended in Tryptone Salt 0.1% diluent) was revived on RBA plates by doing a 3-point inoculation. The inoculated RBA plates were incubated at 30° C. for 36 hours or until the colonies sporulated. The spores were then aseptically sub-cultured onto PDA plates for mass harvesting of the spores. The inoculated PDA plates were then incubated for 30° C. for 36 hours or until the colonies sporulated. Then, the spores were aseptically harvested with a sterile cotton swabs and suspended in sterile Tryptone Salt 0.1% diluent. The suspensions were analyzed for mould spore counts on DG18 plates as well as for microbial contamination on PCA with Cycloheximide by spread plating 0.1-0.5 ml of suspension onto the agar plates respectively. Before the challenge test is initiated, the suspension inoculated with the mould spores was diluted aseptically with sterile Tryptone Salt 0.1% to the desired level such that the inoculation level in the product would be 2-3 log of colony-forming-units (cfu) of moulds per gram of product.

Preparation of Yeasts for CT:

Stock culture of the yeast was revived on MEB. The inoculated broths were incubated at 30° C. for 48-72 hours with constant swirling. The broth cultures were further sub-cultured in the MEB and incubated similarly at 30° C. for 48-72 hours with constant swirling. The final broth cultures were then analyzed for total yeast counts on MEA plate as well as for microbial contamination on PCA by spread plat 0.1-0.5 ml of suspension onto the agar plates respectively. Before the challenge test is initiated, the broth inoculated with yeast was diluted aseptically with sterile Tryptone Salt 0.1% to the desired level such that the inoculation level in the product would be 2-3 log of colony-forming-units (cfu) of yeast per gram (Cfu: colony forming units).

Challenge Tests:

Challenge Test with moulds was according to the following steps: 1) Add 100 g of MOS into a 250 ml sterile Schott bottle with screw-cap cover; 2) Add 0.1 to 2 ml of mould (*A. niger/P. nalgiovence/E. amstelodami*) inoculum to meet the target inoculum of $10^2$-$10^3$ cfu/g of MOS into the 100 g MOS and shake to mix well; 3) Pour 35 g of the inoculated MOS into a petri dish. Perform this in duplicate; 4) Pipette 1 g of inoculated MOS from the Schott bottle into 9 ml sterile Tryptone Salt 0.1% diluents and vortex. Perform this in duplicate; 5) Plate 0.1-0.5 ml of inoculated Tryptone Salt 0.1% onto DG18 plates at appropriate dilutions by Spread Plate Method. Incubate the agar plates at 25° C. for 5 days to enumerate the initial mould count; 6) Incubate the inoculated MOS in petri dishes at 30° C. for a week. Monitor for mould growth by visual observation after one week. Perform this mould growth monitoring for a period of 4 weeks; 7) The control was prepared by repeating steps 3 to 6 without using any inoculum. The control was plated onto PCA with Cycloheximide plates.

Challenge Test with yeasts was according to the following steps: 1) Add 100 g of MOS into a 250 ml sterile Schott bottle with screw-cap cover; 2) Add 0.1 ml to 2 ml of yeast (*Z. bailii*) inoculum to meet the target inoculum of $10^2$ to $10^3$ cfu/g of MOS into the 100 g MOS and shake to mix well; 3) Pour 35 g of the inoculated MOS into two 150 ml sterile disposable polypropylene container with screw-cap cover; 4) Pipette 1 g of inoculated MOS into 9 ml sterile Tryptone Salt 0.1% diluent and vortex. Perform this in duplicate; 5) Plate 0.1 ml to 0.5 ml of inoculated Tryptone Salt 0.1% onto MEA at appropriate dilutions by Spread Plate Method. Incubate the plates at 30° C. for 3 days for the enumeration of the initial yeast count; 6) Incubate the inoculated MOS in 150 ml containers at 30° C. for a week; 7) After one week, repeat steps 4 to 6 for the weekly monitoring of *Z. bailii* growth behavior in MOS. Perform the monitoring for a period of 4 weeks; 8) The control was prepared by repeating steps 3 to 7 without using any inoculum.

Results:

The results are shown in Table 2. There was no growth detected for all un-inoculated control samples, indicating good storage environment. All samples were stable to yeast growth. However, in the absence of any antimicrobial agent, MOS was susceptible to spoilage by moulds. In contrast, mould growth was not detected in the samples containing either KS or garlic EO/W emulsions, demonstrating that the garlic EO/W emulsions were as effective as KS in protecting MOS. Furthermore, the results demonstrated that 0.06 wt % of garlic oil in form of an EO/W emulsion was sufficient to substitute for 0.10% of KS antimicrobial activity. Hence, garlic EO/W can serve as a natural alternative for chemical preservatives in high-volume oyster sauces.

TABLE 2

| Age of Samples | Antimicrobial Agents | Challenge Micro-organisms | Week 0 (Log cfu/g) | Week 1 (Log cfu/g) | Week 2 (Log cfu/g) | Week 3 (Log cfu/g) | Week 4 (Log cfu/g) |
|---|---|---|---|---|---|---|---|
| 0 month | Water | Control | <1.30 | <1.30 | <1.30 | <1.30 | <1.30 |
| | | Z. bailii | 3.544 | <1.00 | <1.00 | <1.00 | <1.00 |
| | | A. niger | 3.114 | VG | VG | VG | VG |
| | | P. nalgiovense | 3.959 | NVG | VG | VG | VG |
| | | E. amstelodami | 1.881 | VG | VG | VG | VG |
| | 0.10% KS | Control | <1.30 | <1.30 | <1.30 | <1.30 | <1.30 |
| | | Z. bailii | 3.544 | <1.00 | <1.00 | <1.00 | <1.00 |
| | | A. niger | 3.114 | NVG | NVG | NVG | NVG |
| | | P. nalgiovense | 4.079 | NVG | NVG | NVG | NVG |
| | | E. amstelodemi | 2.204 | NVG | NVG | NVG | NVG |
| | 0.06% Clove Leaf EO/W | Control | <1.30 | <1.30 | <1.30 | <1.30 | <1.30 |
| | | Z. bailli | 3.255 | <1.00 | <1.00 | <1.00 | <1.00 |
| | | A. niger | 3.041 | NVG | NVG | NVG | NVG |
| | | P. nalgiovense | 3.973 | NVG | NVG | NVG | NVG |
| | | E. amstelodami | <1.3 | NVG | NVG | NVG | NVG |

TABLE 2-continued

| Age of Samples | Antimicrobial Agents | Challenge Microorganisms | Week 0 (Log cfu/g) | Week 1 (Log cfu/g) | Week 2 (Log cfu/g) | Week 3 (Log cfu/g) | Week 4 (Log cfu/g) |
|---|---|---|---|---|---|---|---|
| | 0.15% Clove Leaf EO/W | Control | <1.30 | <1.30 | <1.30 | <1.30 | <1.30 |
| | | Z. bailii | 3.114 | <1.00 | <1.00 | <1.00 | <1.00 |
| | | A. niger | 3.079 | NVG | NVG | NVG | NVG |
| | | P. nalgiovense | 3.959 | NVG | NVG | NVG | NVG |
| | | E. amstelodami | 1.978 | NVG | NVG | NVG | NVG |

VG: growth;
NVG: no growth

Example 5

The antimicrobial efficacy of clove leaf EO/W emulsions in MAGGI Abalone Sauce (MAS) clove leaf oil concentrations at levels of 0.06 wt % and 0.15 wt % in finished products was monitored for a storage period of 12 months. As before in Example 4, potassium sorbate (KS) and water (no antimicrobial) served as positive and negative control samples.

Materials and Methods:

Clove leave oil was from Synthite Industries; the raw materials for producing MAS were from the Nestlé Petaling Jaya factory. All other materials were as described in Example 4.

The method for producing MAS was the same as for the MOS production in experiment 4. The preparation of the microorganism cultures as well as the challenge tests were identical to the ones described in experiment 4 as well.

Results:

The results are shown in Table 3. There was no growth detected for all un-inoculated control samples, indicating good storage environment. MAS (with water, i.e. in absence of an antimicrobial agent) was susceptible to spoilage, as seen in the growth of yeasts and moulds. In contrast, yeast and mould growth was not detected in the samples containing either KS or clove leaf EO/W emulsion, demonstrating that clove leaf EO/W emulsion was as effective as KS in protecting MAS up to a period of 12 months. Hence, the results demonstrated that 0.06 wt % of clove leaf oil in form of an EO/W emulsion was sufficient to substitute for 0.10% of KS antimicrobial activity.

TABLE 3

| Age of Samples | Antimicrobial Agents | Challenge Microorganisms | Week 0 (Log cfu/g) | Week 1 (Log cfu/g) | Week 2 (Log cfu/g) | Week 3 (Log cfu/g) | Week 4 (Log cfu/g) |
|---|---|---|---|---|---|---|---|
| 0 month | Water | Control | <1.00 | <1.00 | <1.00 | <1.00 | <1.00 |
| | | Z. bailii | 2.06 | 4.06 | >4.00 | >4.00 | >4.00 |
| | | A. niger | 1.37 | VG | VG | VG | VG |
| | | P. nalgiovense | 2.56 | VG | VG | VG | VG |
| | | E. amstelodami | 3.1 | VG | VG | VG | VG |
| | 0.10% KS | Control | <1.00 | <1.00 | <1.00 | <1.00 | <1.00 |
| | | Z. bailii | <1.00 | <1.00 | <1.00 | <1.00 | <1.00 |
| | | A. niger | 1.9 | NVG | NVG | NVG | NVG |
| | | P. nalgiovense | 1.54 | NVG | NVG | NVG | NVG |
| | | E. amstelodami | 2.93 | NVG | NVG | NVG | NVG |
| | 0.06% Clove Leaf EO/W | Control | <1.00 | <1.00 | <1.15 | <1.00 | <1.00 |
| | | Z. bailii | <1.72 | <1.00 | <1.00 | <1.00 | <1.00 |
| | | A. niger | 1.69 | NVG | NVG | NVG | NVG |
| | | P. nalgiovense | 2.29 | NVG | NVG | NVG | NVG |
| | | E. amstelodami | 2.51 | NVG | NVG | NVG | NVG |
| | 0.15% Clove Leaf EO/W | Control | <1.00 | <1.00 | <1.00 | <1.00 | <1.00 |
| | | Z. bailii | <1.00 | <1.00 | <1.00 | <1.00 | <1.00 |
| | | A. niger | <1.15 | NVG | NVG | NVG | NVG |
| | | P. nalgiovense | <1.00 | NVG | NVG | NVG | NVG |
| | | E. amstelodami | 1.43 | NVG | NVG | NVG | NVG |
| 1 month | Water | Control | <1.00 | <1.00 | <1.00 | <1.00 | <1.00 |
| | | Z. bailii | 1.58 | 3.99 | >4.00 | <5.64 | >4.00 |
| | | A. niger | 2.05 | VG | VG | VG | VG |
| | | P. nalgiovense | 1.78 | VG | VG | VG | VG |
| | | E. amstelodami | 1.74 | VG | VG | VG | VG |
| | 0.10% KS | Control | <1.00 | <1.00 | <1.00 | <1.00 | <1.00 |
| | | Z. bailii | <1.00 | <1.63 | <1.00 | <1.00 | <1.00 |
| | | A. niger | 1.15 | NVG | NVG | NVG | NVG |
| | | P. nalgiovense | 1.73 | NVG | NVG | NVG | NVG |
| | | E. amstelodami | 1.54 | NVG | NVG | NVG | NVG |
| | 0.06% Clove Leaf EO/W | Control | <1.00 | <1.00 | <1.00 | <1.00 | 1.00 |
| | | Z. bailii | <1.00 | <1.00 | <1.00 | <1.00 | <1.00 |
| | | A. niger | 1.79 | NVG | NVG | NVG | NVG |
| | | P. nalgiovense | 1.5 | NVG | NVG | NVG | NVG |
| | | E. amstalodami | 1.48 | NVG | NVG | NVG | NVG |
| | 0.15% Clove Leaf EO/W | Control | <1.00 | <1.00 | <1.00 | <1.00 | <1.00 |
| | | Z. bailii | <1.00 | <1.00 | <1.00 | <1.15 | <1.00 |
| | | A. niger | 1.15 | NVG | NVG | NVG | NVG |
| | | P. nalgiovense | <1.00 | NVG | NVG | NVG | NVG |
| | | E. amstelodami | <1.15 | NVG | NVG | NVG | NVG |
| 3 month | Water | Control | <1.00 | <1.00 | <1.00 | <1.00 | <1.00 |
| | | Z. bailii | 2.85 | >4.48 | >4.48 | >4.48 | >4.48 |
| | | A. niger | 2.32 | VG | VG | VG | VG |
| | | P. nalgiovense | 2.62 | VG | VG | VG | VG |
| | | E. amstelodami | 2.63 | VG | VG | VG | VG |
| | 0.10% KS | Control | <1.00 | <1.00 | <1.00 | <1.00 | <1.00 |
| | | Z. bailii | 2.96 | <1.00 | <1.00 | <1.00 | <1.00 |
| | | A. niger | 2.19 | NVG | NVG | NVG | NVG |

TABLE 3-continued

| Age of Samples | Antimicrobial Agents | Challenge Microorganisms | Week 0 (Log cfu/g) | Week 1 (Log cfu/g) | Week 2 (Log cfu/g) | Week 3 (Log cfu/g) | Week 4 (Log cfu/g) |
|---|---|---|---|---|---|---|---|
| | | P. nalgiovense | 2.71 | NVG | NVG | NVG | NVG |
| | | E. amstelodami | 2.69 | NVG | NVG | NVG | NVG |
| | 0.06% Clove Leaf EO/W | Control | <1.00 | <1.00 | <1.00 | <1.00 | <1.00 |
| | | Z. bailii | 2.26 | <1.00 | <1.00 | <1.00 | <1.00 |
| | | A. niger | 2.19 | NVG | NVG | NVG | NVG |
| | | P. nalgiovense | 2.79 | NVG | NVG | NVG | NVG |
| | | E. amstelodami | 2.39 | NVG | NVG | NVG | NVG |
| | 0.15% Clove Leaf EO/W | Control | <1.00 | <1.00 | <1.00 | <1.00 | <1.00 |
| | | Z. bailii | <1.00 | <1.00 | <1.00 | <1.00 | <1.00 |
| | | A. niger | 1.86 | NVG | NVG | NVG | NVG |
| | | P. nalgiovense | 2.54 | NVG | NVG | NVG | NVG |
| | | E. amstalodami | 2.04 | NVG | NVG | NVG | NVG |
| 6 month | Water | Control | <1.00 | <1.00 | <1.00 | <1.00 | <1.00 |
| | | Z. bailii | 2.16 | >4.00 | >4.00 | >4.00 | >4.00 |
| | | A. niger | 2.19 | VG | VG | VG | VG |
| | | P. nalgiovense | 2.00 | VG | VG | VG | VG |
| | | E. amstelodami | 2.81 | VG | VG | VG | VG |
| | 0.10% KS | Control | <1.00 | <1.00 | <1.00 | <1.00 | <1.00 |
| | | Z. bailii | 2.13 | <1.00 | <1.00 | <1.00 | <1.00 |
| | | A. niger | 2.16 | NVG | NVG | NVG | NVG |
| | | P. nalgiovense | 2.03 | NVG | NVG | NVG | NVG |
| | | E. amstelodami | 2.67 | NVG | NVG | NVG | NVG |
| | 0.06% Clove Leaf EO/W | Control | <1.00 | <1.00 | <1.00 | <1.00 | <1.00 |
| | | Z. bailii | 3.96 | <1.00 | <1.00 | <1.00 | <1.00 |
| | | A. niger | 2.28 | NVG | NVG | NVG | NVG |
| | | P. nalgiovense | 1.95 | NVG | NVG | NVG | NVG |
| | | E. amstelodami | 2.72 | NVG | NVG | NVG | NVG |
| | 0.15% Clove Leaf EO/W | Control | <1.00 | <1.00 | <1.00 | <1.00 | <1.00 |
| | | Z. bailii | <1.00 | <1.00 | <1.00 | <1.00 | <1.00 |
| | | A. niger | 1.95 | NVG | NVG | NVG | NVG |
| | | P. nalgiovense | 2.1 | NVG | NVG | NVG | NVG |
| | | E. emstelodami | 2.52 | NVG | NVG | NVG | NVG |
| 10 month | Water | Control | <1.00 | <1.00 | <1.00 | <1.00 | <1.00 |
| | | Z. bailii | 4.11 | >4.176 | 6.83 | 6.41 | 5.81 |
| | | A. niger | 3.58 | VG | VG | VG | VG |
| | | P. nalgiovense | 4.41 | NVG | VG | VG | VG |
| | | E. amstelodami | 3.91 | VG | VG | VG | VG |
| | 0.10% KS | Control | <1.00 | <1.00 | <1.00 | <1.00 | <1.00 |
| | | Z. bailii | 4.43 | <2.00 | <1.00 | <1.00 | <1.00 |
| | | A. niger | 3.67 | NVG | NVG | NVG | NVG |
| | | P. nalgiovense | 3.86 | NVG | NVG | NVG | NVG |
| | | E. amstelodami | 3.80 | NVG | NVG | NVG | NVG |
| | 0.06% Clove Leaf EO/W | Control | <1.00 | <1.00 | <1.00 | <1.00 | <1.00 |
| | | Z. bailii | 2.60 | <2.00 | <1.00 | <1.00 | <1.00 |
| | | A. niger | 3.48 | NVG | NVG | NVG | NVG |
| | | P. nalgioveme | 3.84 | NVG | NVG | NVG | NVG |
| | | E. amstelodami | 3.72 | NVG | NVG | NVG | NVG |
| | 0.15% Clove Leaf EO/W | Control | <1.00 | <1.00 | <1.00 | 1.00 | 1.00 |
| | | Z. bailii | <2.00 | <2.00 | <1.00 | <1.00 | <1.00 |
| | | A. niger | 2.32 | NVG | NVG | NVG | NVG |
| | | P. nalgiovense | 2.28 | NVG | NVG | NVG | NVG |
| | | E. amstelodami | 2.81 | NVG | NVG | NVG | NVG |
| 12 month | Water | Control | <1.00 | <1.30 | <1.30 | <1.30 | <1.30 |
| | | Z. bailii | 3.15 | 6.59 | 6.73 | 7.08 | 6.90 |
| | | A. niger | 2.38 | VG | VG | VG | VG |
| | | P. nalgiovense | 3.60 | VG | VG | VG | VG |
| | | E. amstelodami | 2.41 | VG | VG | VG | VG |
| | 0.10% KS | Control | <1.00 | <1.30 | <1.30 | <1.30 | <1.30 |
| | | Z. bailii | 2.84 | 1.72 | <1 | <1 | <1 |
| | | A. niger | 2.96 | NVG | NVG | NVG | NVG |
| | | P. nalgiovense | 3.26 | NVG | NVG | NVG | NVG |
| | | E. amstelodami | 2.38 | NVG | NVG | NVG | NVG |
| | 0.06% Clove Leaf EO/W | Control | <1.00 | <1.30 | <1.30 | <1.30 | <1.30 |
| | | Z. bailii | 2.04 | <1 | <1 | <1 | <1 |
| | | A. niger | 2.92 | NVG | NVG | NVG | NVG |
| | | P. nalgiovense | 3.23 | NVG | NVG | NVG | NVG |
| | | E. amstelodami | 1.95 | NVG | NVG | NVG | NVG |
| | 0.15% Clove Leaf EO/W | Control | <1.00 | <1.30 | <1.30 | <1.30 | <1.30 |
| | | Z. bailii | <1.30 | <1.00 | <1.00 | <1.00 | <1.00 |
| | | A. niger | 2.56 | NVG | NVG | NVG | NVG |
| | | P. nalgiovense | 3.18 | NVG | NVG | NVG | NVG |
| | | E. amstelodami | <1.3 | NVG | NVG | NVG | NVG |

VG: growth;
NVG: no growth

The invention claimed is:

1. A method for providing an antimicrobial effect in an aqueous composition, the method comprising adding to an aqueous composition (i) an antimicrobial essential oil present in a concentration of less than 0.08 wt % of the aqueous composition, (ii) acacia gum and (iii) water, wherein the essential oil is selected from the group consisting of oregano oil, garlic oil, ginger oil, lime oil, lemon oil, lemongrass oil, and citrus oil, and combinations thereof.

2. The method of claim 1, wherein the aqueous composition is selected from the group consisting of a beverage, a food product, a food supplement and an aliment for animals.

3. The method of claim 1, wherein the essential oil is selected from the group consisting of oregano, garlic oil, and combinations thereof.

4. A process to improve the antimicrobial effect of an antimicrobial essential oil, the process comprising:
   emulsifying the essential oil with acacia gum and water to form an emulsion, wherein the essential oil is selected from the group consisting of oregano oil, garlic oil, ginger oil, lime oil, lemon oil, lemongrass oil, and citrus oil, and combinations thereof; and
   adding the emulsion to an aqueous composition to result in a final concentration of the essential oil in the aqueous composition of less than 0.08 wt %,
   wherein the weight ratio of the essential oil to acacia gum is from 1:0.5 to 1:50.

5. The process of claim 4, wherein the essential oil is selected from the group consisting of oregano, garlic oil, and combinations thereof.

6. A process to improve the antimicrobial effect of an antimicrobial essential oil, the process comprising:
   adding the essential oil and acacia gum to an aqueous composition to result at a final concentration of the essential oil in the aqueous composition of less than 0.08 wt %; and
   mixing the aqueous composition in order to emulsify the essential oil with the acacia gum,
   wherein the essential oil is selected from the group consisting of oregano oil, garlic oil, ginger oil, lime oil, lemon oil, lemongrass oil, and citrus oil, and combinations thereof, and
   wherein the weight ratio of the essential oil to acacia gum is from 1:0.5 to 1:50.

7. The process of claim 6, wherein the essential oil is selected from the group consisting of oregano, garlic oil, and combinations thereof.

\* \* \* \* \*